United States Patent [19]

Brehm

[11] Patent Number: 5,067,495

[45] Date of Patent: Nov. 26, 1991

[54] ELECTRO WAVE THERAPY

[76] Inventor: Richard L. Brehm, Rte. 9, Box 205B, Chippewa Falls, Wis. 54729

[21] Appl. No.: 516,353

[22] Filed: Apr. 30, 1990

Related U.S. Application Data

[63] Continuation-in-part of Ser. No. 413,276, Sep. 27, 1989, abandoned.

[51] Int. Cl.$^5$ .............................................. A61N 1/18
[52] U.S. Cl. .............................. 128/421; 128/423 W
[58] Field of Search .................. 128/421, 422, 423 R, 128/423 W, 420 A

[56] References Cited

U.S. PATENT DOCUMENTS

| | | | |
|---|---|---|---|
| 3,902,502 | 9/1975 | Liss | 128/421 |
| 3,911,930 | 10/1975 | Hagfors et al. | 128/421 |
| 4,023,574 | 5/1977 | Nemec | 128/421 |
| 4,147,171 | 4/1979 | Greene et al. | 128/421 |
| 4,155,366 | 5/1979 | Di Mucci | 128/421 |
| 4,431,000 | 2/1984 | Butler et al. | 128/421 |
| 4,848,347 | 7/1989 | Hall | 128/420 A |

FOREIGN PATENT DOCUMENTS 3442760A  6/1985  Fed. Rep. of Germany.

OTHER PUBLICATIONS

A 1979 article by Erickson, Sjolund and Nielzen titled Long Term Results of Peripheral Conditioning Stimulation as an Analgesic Measure in Chronic Pain.
Roth and Thras in the 1985 *American Journal of Orthodontics*, vol. 90, No. 2, pp. 132–138.
An article by Rober Ersek in the *Orthopaedic Review*, vol. V, No. 12, Dec. 1976 titled Low Back Pain: Prompt Relief with Transcutaneous Neuro-Stimulation.
A 1979 article by Mannheimer and Carlsson titled The Analgesic Effect of Transcutaneous Electrical Nerve Stimulation (TNS) in Patients with Rheumatoid Arthritis, A Comparative Study of Different Pulse Patterns.
A 1979 article by Sjolund and Erickson titled Endorphins and Analgesia Produced by Peripheral Conditioning Stimulation, published in *Advances in Pain Research and Therapy*, vol. 3, pp. 587 to 592.

*Primary Examiner*—William E. Kamm
*Assistant Examiner*—Scott M. Getzow
*Attorney, Agent, or Firm*—Jacobson & Johnson

[57] ABSTRACT

A method of treatment of pain to provide permanent pain relief in a patient by applying an electrical signal having the shape of a monophasic wave across the region of a patient that is perceiving pain for an extended period of time to relieve the pain and permitting the patient to adjust the electrical signal to maintain a constant level of feeling in the treated area.

19 Claims, 3 Drawing Sheets

ELECTRO WAVE THERAPY

CROSS REFERENCE TO RELATED APPLICATIONS

This application is a continuation in part of my patent application U.S. Ser. No. 413,276 titled ELECTRO WAVE THERAPY, filed Sept. 27, 1989 now abandoned.

FIELD OF THE INVENTION

This invention relates generally to treatment of pain and, more specifically, to electrical stimulus of the body to relieve chronic pain.

BACKGROUND OF THE INVENTION

The concept of treatment of pain through application of electrical signals to the body is known in the art. One such electrical stimulator that is on the market today is sold by the Empi, Inc. of Minneapolis, Minn. Briefly, the concept of such prior art units for treating pain is to apply an electrical signal across electrodes located on the user's body by applying a first electrode directly on the site of pain on the user and a second electrode between the site of pain and the user's head. The believed principal of operation behind such prior art electrical stimulator units are to provide an interruption of the pain signal from the pain site to the brain. Usually, such units only provide temporary relief to the person suffering from the pain.

Still others have the tester control the level of stimulation to the area where the pain is perceived to emanate from. In other applications the wave forms, the frequencies, and the voltage have been controlled to determine the effectiveness of the treatment.

Generally, there are two major types of pain that patients suffer from, acute pain and chronic pain. Acute pain is generally pain of short duration, with severe intensity, such as accompanied by surgery or ileitis. Acute pain if left untreated will gradually disappear with no further treatment. Chronic pain on the other hand is pain of a long duration that has defied any type of treatment to eliminate the pain. Most chronic pain is of several months or years of duration. Although with chronic pain the intensity of the pain may vary from time to time the body incapable of healing it self to eliminate the chronic pain. Treatment for chronic pain has generally been ineffective since if the pain responds to a treatment the pain generally reappears in a short time. The present invention is directed toward the treatment of chronic pain in patients who have suffered with chronic pain for many months or years.

The present invention provides a patient responsive treatment for chronic pain that has been found to result in greater long term effectiveness than other methods and to produce pain relief in patients who have not responded to prior electrical stimulation treatment. In the present method of treatment the patient applies an electrical signal having a monophasic wave form across but not on the area of the body where the user perceives the pain for a predetermined length of time which often results in permanent pain relief in the patients. The present invention relies on the patient control of the voltage level of a particular type of electrical signal applied to the appropriate area of the patients body to provide permanent pain relief to the patient. Thus the feedback from the patients body feeling is used directly by the patient to control the level of the electrical signal applied to electrodes. This type of feedback treatment combined with an electrical signal having a monophasic wave form has been found to be generally superior method for the treatment of pain in a patient.

DESCRIPTION OF THE PRIOR ART

The Hagfors U.S. Pat. No. 3,911,930 shows apparatus and method for treatment of acute pain that results from a trauma such as surgery or the like. Hagfors places the electrodes across and parallel to the incision. The purpose of Hagfors is to reduce the acute pain so that normal body functions such as deep breathing and coughing can return more quickly. No contention is made that the Hagfors treatment would or could be used with treatment of chronic pain. Hagfors does not use a monophasic wave but instead uses a single positive pulse having a width of 200 to 400 milliseconds with a frequency ranging from 10 to 300 pules per second. Hagfors also points out that his electrodes should have a surface area greater than 3 square inches.

The Mucci U.S. Pat. No. 4,155,366 shows a device that the user can carry on his or her person and adjust the voltage to the desired level. Mucci generates a sawtooth waveform in the range of 10 HZ to 100 HZ with a voltage amplitude in the range of 1 to 100 volts. The first electrodes is placed on the portion of the body experiencing pain and the other electrodes is located within seven to twenty centimeters of the first electrode.

The Butler et al. U.S. Pat. No. 4,431,000 discloses a transcutaneous electrical nerve stimulator for use in treating a a patient having a neurologically based speech and language impairment such as aphasia. Butler produces a pulse train of varying rate that is generated by a random pulse generator.

The Nemec U.S. Pat. No. 4,023,574 describes a treatment where various sets of electrodes are applied to an organ with the main frequently of the alternating current ranging from 1000 HZ to 100,000 HZ and a secondary frequency differing from the first frequency by about 100 HZ.

The Liss U.S. Pat. No. 3,902,502 shows a portable device for providing temporary pain relief for one to eight hours. Liss uses a pulsed dc current ranging from 20 kilohertz to one megahertz.

The German patent 3442-760-A discloses an electrotherapy-massage apparatus that periodically dispense a sine wave carrier with a frequency ranging from 1100 to 1500 Hertz with a modulating frequency of 30-45 cycles per minute.

An article by Rober Ersek in the *Orthopaedic Review* Volume V No. 12 December 1976 titled *Low Back Pain: Prompt Relief with Transcutaneous Neuro-Stimulation* describes the application of electrical stimulation directly upon the dorsal column by implanted electrodes.

An article by Roth and Thrash in the 1985 *American Journal of Orthodontics*, Volume 90 No. 2 pp 132-138 describes how Transcutaneous electrical nerve stimulation can be used with patients to control pain resulting from the adjustment of orthodontic appliances.

A 1979 article by Mannheimer and Carlsson titled *The Analgesic Effect of Transcutaneous Electrical Nerve Stimulation (TNS) in Patients with Rheumatoid Arthritis. A comparative Study of different Pulse Patterns* describes the use of different pulse patterns to treat wrist pain due to rheumatoid arthritis. Frequencies of 70 HZ and 3 HZ were used in the treatment.

A 1979 article by Erickson, Sjolund and Nielzen titled *Long Term Results of Peripheral Conditioning Stimulation as an Analgesic Measure in Chronic Pain* describes how patients were treated transcutaneous nerve stimulation with a signal ranging from 10 to 100 HZ.

A 1979 article by Sjolund and Erickson titled *Endorphins and Analgesia Produced by Peripheral Conditioning Stimulation*, published in *Advances in Pain Research and Therapy* Volume 3 pages 587 to 592 describes how electroacupuncture is used to treat patients but is of limited value in treatment of patients with chronic pain.

BRIEF SUMMARY OF THE INVENTION

Figure 1:
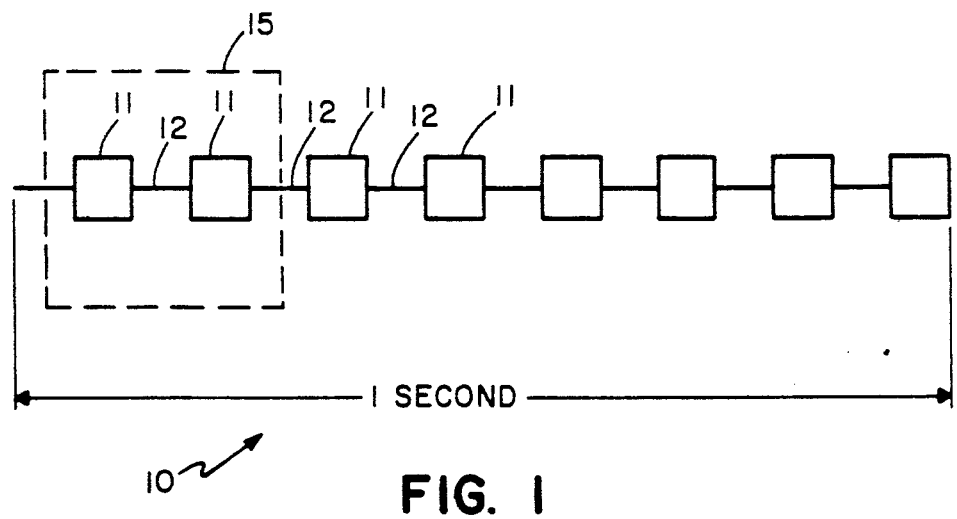
FIG. 1 shows a schematic of an electrical signal in the form of a monophasic wave that is used with the electro wave treatment of my invention.

Briefly, the present invention comprises a method of treatment of chronic pain to a user having an area of the body that is responsible for the pain that includes; applying a first electrode to the body with the electrode spaced from the area of the body that is responsible for the pain; applying a second electrode to the body with the second electrode spaced from the area of the body that is responsible for the pain; and then applying an electrical signal with a monophasic wave form across the electrodes for a period of time sufficient to establish pain relief.

DESCRIPTION OF THE PREFERRED METHOD

The electro wave therapy or electro wave treatment of the present invention involves the use of a device that can generate an electrical wave form that is known as a monophasic wave form. The devices for generation of electrical signals having a monophasic wave form or the like is well known in the art. Such prior art units are sold and identified in the marketplace as T.E.N.S. units (transcutaneous electrical nerve stimulator). While the prior art units for generating an electrical signal with a monophasic wave form have been known the use of electrical signals with monophasic wave forms have been generally ineffective in treatment of pain in a user. That is the in conventional treatment of pain with a prior art T.E.N.S. unit one places one electrode on the pain site on the body and another electrode on the body between the pain site and the patients head. In the present invention the placement of the electrodes is spaced from but proximate to the pain site so that the electrical signal with the monophasic wave form can be applied substantially directly across the region where the patient perceives the pain.

Briefly, the present invention comprises a method of patient responsive treatment of chronic pain in a patient with transcutaneous electrical nerve stimulation on an area of the body where the patient perceives pain. Treatment involves using an electrical signal having a monophasic wave form. In the first step one applies a first electrode to the body with the first electrode adjacent to but spaced from the area of the body where the patient perceives the pain. The user then applies a second electrode to the body with the second electrode adjacent to but spaced from the area of the body where the patient perceives the pain. The electrodes are spaced across the area of the body where the patient perceives the pain but not on the area of the body where the patient perceives the pain. The tester then instructs the patient to adjust the level of voltage directed across the electrodes until a constant level of uncomfortableness but not a painful feeling is maintained in the area of the body being treated. The patient is then allowed to apply and control the electrical signal having a monophasic wave form across the electrodes in accordance with the patients feeling in the area of the body where the patient perceives pain. The patient maintains the electrical signals having a monophasic wave form on the body site where the pain is perceived for a minimum time of about thirty minutes to thereby induce a long term pain relief in the area where the patient perceives pain. If after treatment no redness is observed in the region of the skin located directly below the electrodes the patient is asked to repeat the procedure and encouraged to increase the voltage levels.

An electrical signal in the form of a monophasic wave form 10 is generally shown in schematic form in FIG. 1. Monophasic wave 10 comprises a series of sequential burst cycles comprised of a wave burst and a pause. I have generally found that if the frequency of burst cycles range from about 8 to 10 burst cycles per second I can obtain good results with my treatment method. The wave burst portion of the electrical signals are identified by reference numeral 11. Each wave burst 11 is followed by a pause of no electrical signal that is identified by reference numeral 12. Together wave burst 11 and pause 12 make up the wave burst cycle portion of monophasic wave 10.

Figure 2:
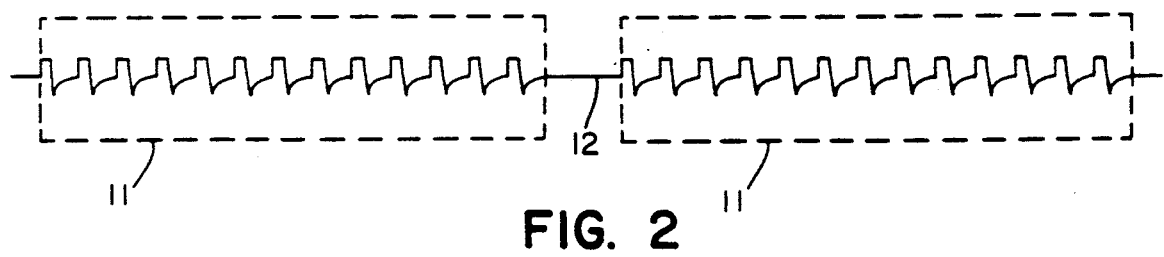
FIG. 2 shows a burst cycles of an electrical wave contained within the monophasic wave of FIG. 1.

FIG. 1 shows wave burst 11 and pause signal 12 enclosed within a dotted box 15. FIG. 2 illustrates the typical sequence of an individual wave in each burst cycle. In the wave form shown each wave burst includes 13 separate waves. In generally, I have found that a frequency of 13 to 18 waves per burst have been effective in reducing or eliminating pain to a person being treated with the method of my invention.

Figure 3:
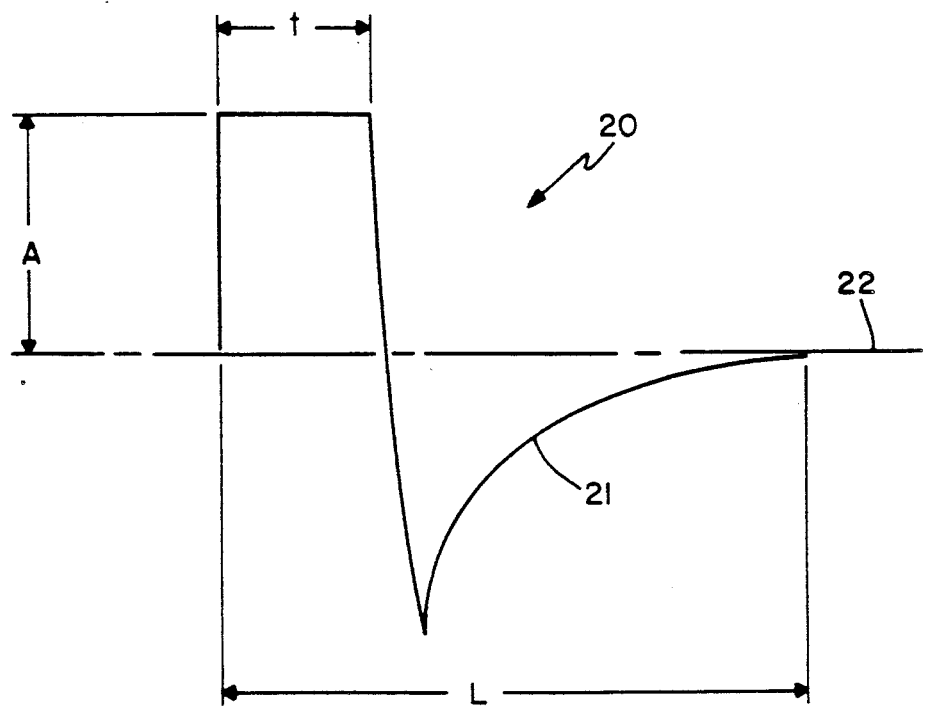
FIG. 3 shows an individual wave forming part of the monophasic wave.

FIG. 3 illustrates the typical shape of each wave 20 in each of the wave bursts. Wave 20 has an amplitude denoted by A, a duration of a square positive pulse identified by t and a negative portion 21 located below the zero signal line 22. The shape and duration of the waves in the monophasic wave form may vary but in general the monophasic wave form takes the shape as identified in FIG. 1, FIG. 2, and FIG. 3. It should be understood that the general monophasic wave shape for an electrical signal is known in the art and the purposes of the drawings is to generally identify the different portions of the electrical signal having a monophasic wave form.

Typically, the positive portion of an individual wave may have a duration time t of approximately 190 microseconds, with each positive portion of the wave having a value of approximately 100 milliamps for delivery to the patient. Since the resistance of the patients skin may vary it has been found appropriate to identify the electrical signal applied to the patient in terms of amperage rather than in terms of voltage.

Figure 4:
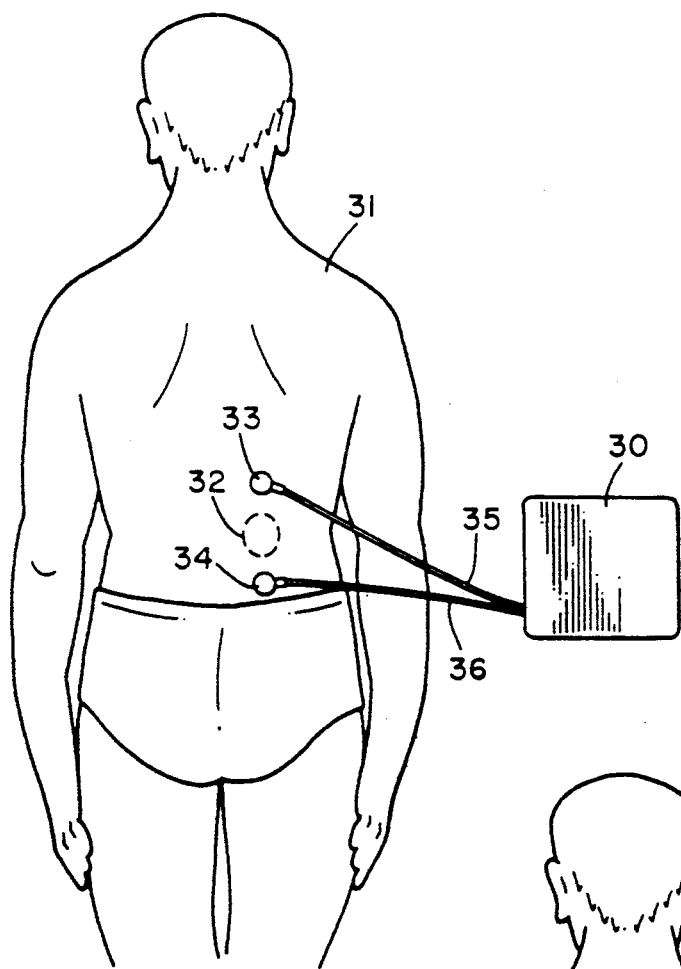
FIG. 4 shows the present invention being used to apply an electrical signal to the regions above and below the pain site.

In order to understand the operation of my invention to relieve pain in a user reference should be made to FIG. 4 which shows a prior art electrical stimulator 30 for generating an electrical signal in the form of a monophasic wave. The patient is identified by reference numeral 31 with the region of pain on patient identified by the dotted region 32.

In the present treatment method I apply a first gel coated black carbon-rubber electrode 33 directly to the skin in the body area above pain site 32. I apply a second gel coated black carbon electrode 34 in the body area on the opposite side of pain site 32. Electrode 33 connects to the electrical stimulator 30 through a flexible electrical wire 35. Similarly, electrode 34 connects to electrical stimulator 30 through flexible electrical wire 36. Electrical stimulator 30 includes a control to regulate the amount of current being delivered to the electrodes (not shown). In general the electrodes are spaced on opposites sides of the pain region and are spaced proximate to the pain region but not directly on the pain region. In some cases where the pain may occur in two separate but adjacent regions of the body the electrodes may be spaced on opposite sides of both pain regions.

In general we have found that if the diameter of the electrodes is about 15 millimeters or less one obtains excellent results. The limitation on the size of the electrodes is the convenience in handling and ability to tape the small electrode to the patient although current evaluation suggest that even smaller electrodes would be more effective.

Once the electrodes are applied to the skin the operator turns the electrical stimulator 30 on for a period of time to produce an effective relief of pain in the patient. In most cases a treatment of about 30 minutes provides excellent results. However, some individuals body may react differently to the strength or duration of the treatment. In some cases the amount of current supplied during each wave burst may have to be reduced or increased. That is some patients may not be able to tolerate voltage signals producing waves with 15 milliamps while others may tolerate up to 100 milliamps without any discomfort. If the treatment for thirty minutes with waves of approximately 100 milliamps does not produce the desires pain relief the operator may have to repeat the treatment at a later date. In other cases the tolerance of the electrical signal to provide the necessary treatment may have to be determined by varying the amperage and the duration until the patient body responds positively.

Figure 5:
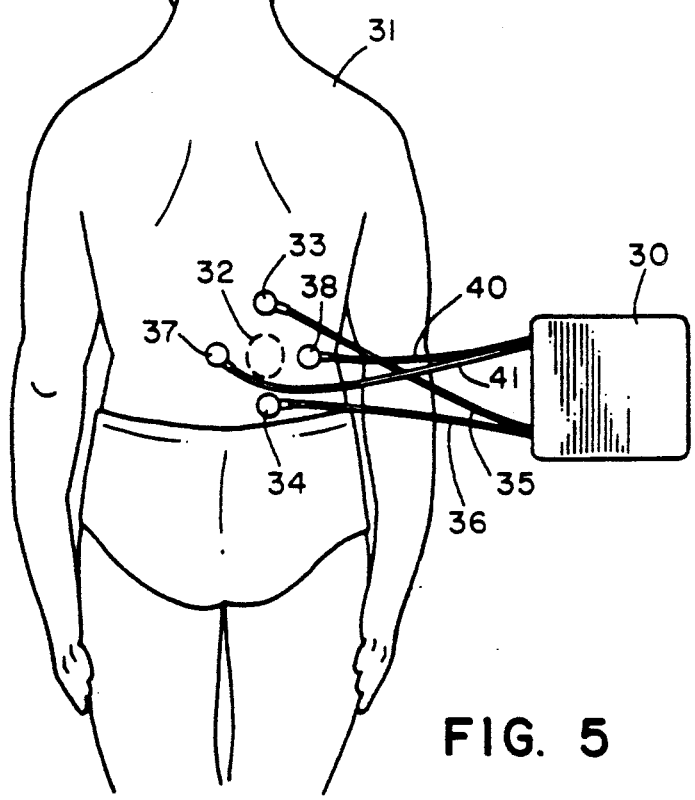
FIG. 5 shows an alternate method of applying an electrical signal to the pain site of a user.

Referring to FIG. 5 there is shown how one can proved electro wave therapy with an electrical stimulator producing two separate electrical signals each having a monophasic wave form. A patient 31 having four electrodes connected around the pain site is shown. In addition to the electrodes 33 and 34 which are located above and below pain site 32 that provide a separate electrical signal I provide two additional electrodes 37 and 38 that are also spaced away form the pain 32. Electrodes 37 and 38 are connected to electrical stimulator which send an identical but separate electrical of monophasic form which is out of phase with the first electrical signal applied across electrodes 33 and 34. That is, by having the electrical signals out of phase the patient only receives an electrical signal from one set of electrodes at a time.

Figure 6:
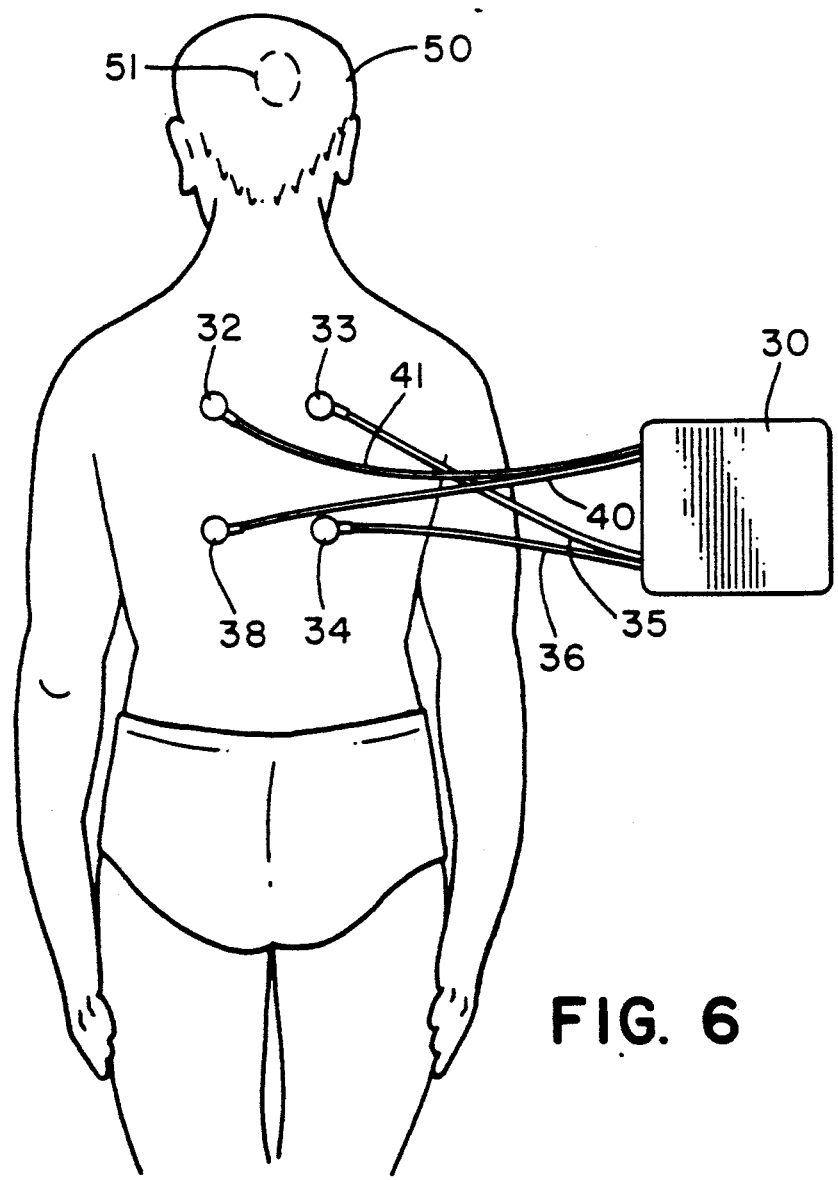
FIG. 6 shows a further alternate method for treatment of a pain such as occurs in a headache.

While most pain regions are treated by spacing the electrodes from the pain region and generally applying the electrodes along the direction of contraction and relaxation of the muscles there are certain applications where the electrodes may not be spaced directly across the pain region. FIG. 6 illustrates a person 50 who is suffering from a headache. Typically, the pain from a headache is perceived by the patent to be emanating some place from the persons head and is identified as region 51. Treatment of a pain such as one perceived from coming from region 51 surprisingly, can be accomplished by applying an electrical stimulus through electrodes located in the upper back region of the person. It is not fully understood why the application of two electrical signals in the form of monophasic wave shape or the like through electrodes 33, 34, 37, and 38 to the upper back region of the user to a region that is remote from the perceived pain site provides relief. However, experiments have been found that such application of the an electrical signal of monophasic wave form produces relief from headache. It should be pointed out that my invention only requires treatment for a short period of time whereas with prior units pain relief usually only occurs when the electrical signal is applied to the user.

While the full mechanism of how my invention of electro wave therapy operates to relieve pain is not fully understood my method has been found effective in treatment of muscle disorder, joint disorders, headaches, and post-surgical pain ranging from head to foot.

In evaluating my process a number of people suffering from pain were asked to evaluate the therapy in terms of pain relief. In one case a person complaining of stiffness was also treated. In each case the patient was allowed to control the amount of voltage applied by adjusting the voltage to the level the patient felt was uncomfortable but not painful. That is, the patients were asked to adjust the voltage level to maintain a constant level of feeling in the treated area which was above a certain threshold but below a level of pain induced by the voltage.

Although the level of applied voltage was monitored by the tester no guidance was given as to what level of voltage may be appropriate for the patient. By use of individual control of the voltage it was believed one can minimize the differences in patient skin resistance. The method of allowing the patient to control the voltage in some cases caused the patients to provide to low voltages for proper treatment. Patients who used inadequate voltages usually could be detected by observing the region of the skin directly beneath the electrode after the patient had completed the treatment. If the skin showed redness the level of voltage was adequate but if no redness was present after the electrodes were removed the level of voltage was usually inadequate and the patients were instructed to repeat the treatment using higher voltages. In cases where the patients were asked to repeat the tests with higher voltages usually favorable results were obtained with higher levels of voltages. However, for test results to be independent of acquired patient familiarity with the equipment and to validate the test procedure only the patient pain relief for first tests was included in the test results even tho subsequent treatment brought substantial pain relief.

Before proceeding with the therapy the electrodes were spaced on opposite sides of the area of the body where the patient perceived the pain but not directly on the area of the body where the patient perceived the pain to be originating form. To record the pain relief each patient was given a sheet of paper with a 10 centimeter scale and told that the left end of the scale (0) represented no pain and the right end of the scale (10) represented maximum pain. The patient was then asked to draw a vertical line to represent the level of pain before treatment. After the first treatment was completed, which lasted 30 minutes, the patient was asked to draw a second vertical line on the scale to indicate the level of pain after treatment. The differences in the patients pain before and after treatment were compared to obtain a percentage reduction in pain.

Ninety nine patients were treated with one patient indicating an increase of pain after treatment. It was not determined why one person had an adverse response but may have been due to the patient not being able to properly administer the treatment or the peculiarities of the patients pain. It should be pointed out that such an adverse reaction in isolated cases is not unexpected since other testers using different treatment methods with transcutaneous neurostimulation have noted an adverse response which they believe is due to stimulation of the large fibers which carry pain sensations. Of the remaining ninety eight patients seven indicated pain relief of 5% or less. The remaining patients exhibited pain relief ranging from 9% to 100%.

It should be pointed out that only the pain relief was recorded on the first treatment even tho later treatments would further reduce the level of pain in the patient. It was felt that the comparative results would be less affected by interaction between the patient and the tester if the results were limited to only the first encounter with the electro wave therapy treatment. Also the initial electrode placement was not altered, although later placement of electrodes indicates that in certain cases a displacement of as little as a ¼ inch of the electrodes can result in 40% to 50% reduction in the pain level. The patients were asked to control the voltage level and adjust the voltage level to maintain the voltage at an uncomfortable but not painful level in the treated area.

The results of pain relief are summarized below.

| AREA TREATED | % PAIN RELIEF | |
|---|---|---|
| Arm | 89% | |
| Back | 83% | |
| Elbow | 76% | |
| Foot | 49% | |
| Forehead | 71% | |
| Heel | 81% | increase |
| Hip | 62% | |
| Knee | 70% | |
| Leg | 100% | |
| Low back | 58% | |
| Mid back | 75& | |
| Neck | 70% | |
| Neck and Shoulder | 46% | |
| Shoulder | 51% | |
| Stiffness | 93% | |
| Wrist | 93% | |

Of the patients receiving pain relief from the electro wave therapy the pain reduction ranged from days to permanent in some patients. In those patients that had pain after treatment it was found that in general subsequent repeating of the electro wave therapy would continue to reduce the level of pain and in some cases continued treatment eliminated the pain completely.

The following is a summary of the results of my treatment to five different individuals who suffered from chronic pain.

PATIENT A

Patient A is a male 65 years of age. After open heart surgery two years ago the patient encountered severe neck, arm and chest pain. No relationship to the surgery could be found. Many types of medication were tried with no success. The patient was placed on a conventional T.E.N.S. unit for control of pain but no results were noted. After treatment with my method the arm and the neck pain disappeared with only a slight tingling remaining in two fingers. The chest pain which was so severe that the patient couldn't place a pencil in his pocket without leaning forward, was reduced to the point it could be detected only with firm pressure.

PATIENT B

Patient B is a male 63 years of age. The patient had chronic pain ranging from the neck to the shoulders to the back area. During a normal year the patient is admitted to a hospital to three times for a flare up in the chronic condition. The patent has tried ultrasound, T.E.N.S. and acupuncture treatment with no real relief. After being treated with my method the patient has had his pain problems resolved and has not returned to the hospital.

PATIENT C

Patient C is male 73 years of age. The patient has had chronic pain in his right ankle for fifty five years. The pain is a result of a football injury. During a game a player ran into his foot causing the initial injury. During the following years all forms of treatment proved ineffective. The pain in the ankle increased to a point where all that could be tolerated were short walks. After treatment with my method the patient has been able to resume normal activities such as shopping in the mall with his wife. The patient also reported that he was now able to dance with his wife which he had been unable to do for the past twenty years.

PATIENT D

Patient D is male 73 years of age. The patient suffered four years with a severe pain on the right side of his face which appears to be caused by the fifth nerve. The patient received treatment with a T.E.N.S. unit but received no relief. In order to kill the pain the patient received an alcohol injection which resulted with two years without pain. When the pain returned the patient was advised that the only treatment for his pain was surgery. After treatment with my method the patient reported that the pain was no longer present.

PATIENT E

Patient E is a female thirty years of age. Her occupation is a registered nurse. About five and one half years ago the patient was involved in an automobile accident. From the time of the accident she has had increasing pain with loss of function. The loss includes the inability to lift her arms above shoulder height without the loss of her pulse. She was not able to return to her profession or do simple household chores without suffering severe pain. Consequently, the patient was limited to sitting and doing nothing to avoid the severe pain. The patient had therapy treatment, medication treatment, and acupuncture treatment. The acupuncture treatment produces slight improvement until the last treatment resulted in a severe setback. After treatment with my method the patient condition improved to the point where she no longer needed to take the pain medication. After further treatment the the patient was able to raise and sleep with her arms over head without loss of pulse. The patient has now returned to her profession as a registered nurse.

I claim:

1. A method of treatment of chronic pain to a user having an area of the body that is responsible for the pain comprising the steps of:

applying a first electrode to the body with said first electrode spaced from the area of the body that is responsible for the chronic pain;

applying a second electrode to the body with said second electrode spaced from the area of the body that is responsible for the chronic pain;

applying an electrical signal having a monophasic wave form comprising a series of sequential wave burst cycles, said wave burst cycles including a wave burst having individual waves each having a positive pulse followed by a negative pulse with each of the sequential wave bursts followed by a pause, said electrical signal applied across said electrodes to thereby direct the electrical signal having the monophasic wave form into the body for a period of time sufficient to relieve the chronic pain in the body after the treatment has been terminated.

2. The method of claim 1 wherein the user controls the electrical signal by adjusting the voltage to maintain a constant level of feeling in the chronic pain area.

3. The method of claim 2 wherein the user applies the electrical signal for a minimum of thirty minutes.

4. The method of claim 1 wherein said electrodes are placed on opposite sides of the chronic pain area on the body.

5. The method of claim 4 wherein the site of chronic pain is in a muscle that has a pathway for contraction and relaxation and said electrodes are placed on opposites sides of the site of the chronic pain and along the pathway of contraction and relaxation of the muscle.

6. The method of claim 1 wherein the electrical signal is applied to the area of the body responsible for the chronic pain for approximately thirty minutes.

7. The method of claim 1 wherein at least four electrodes are applied to the area of the body responsible for the chronic pain with said electrodes being spaced from each other and from the area of the body that is responsible for the chronic pain.

8. The method of claim 7 wherein two separate electrical signals are applied to the electrodes.

9. The method of claim 7 wherein two separate electrical signals are applied to the body with one of said electrical signals being out of phase with the other so that the body only receives one electrical signal at a time.

10. The method of claim 1 wherein one applies the electrical signal having a wave burst cycle frequency of approximately 8 to 10 wave burst cycles per second.

11. The method of claim 10 wherein one applies the electrical signal having approximately 13 to 18 individual waves per wave burst for approximately thirty minutes.

12. The method of claim 11 wherein the individual waves of the electrical signal have a frequency rate that is less than 2500 waves per second.

13. The method of claim 1 wherein the monophasic wave has positive pulses of a duration of approximately 190 microseconds followed by a negative pulse.

14. The method of claim 1 wherein the amplitude of the monophasic wave is less than 100 milliamps.

15. The method of claim 1 wherein said electrodes have a diameter of 15 millimeters or less.

16. A method of patient responsive treatment of chronic pain to a patient with transcutaneous electrical nerve stimulation on an area of the body where the patient perceives chronic pain through use of an electrical signal having a monophasic wave form comprising the steps of:

applying a first electrode to the body with said first electrode adjacent to but spaced from the area of the body where the patient perceives the chronic pain;

applying a second electrode to the body with said second electrode adjacent to but spaced from the area of the body where the patient perceives the chronic pain so that said first electrode and said second electrode are spaced across the area of the body where the patient perceives the chronic pain but not on the area of the body where the patient perceives the chronic pain;

having the patient adjust the level of voltage directed across the first and second electrodes until a constant level of feeling is maintained in the area of the body of the patient being treated; and then the patient controlling the electrical signal having a monophasic wave comprising a series of sequential wave burst cycles, said wave burst cycles including a wave burst having individual waves, each individual wave having a positive pulse followed by a negative pulse with each of the sequential wave bursts followed by a pause, said electrical signal applied across said electrodes in accordance with the feeling in the area of the body of the patient where the patient perceives chronic pain with the patient maintaining the electrical signals having a monophasic wave form into the body site where the chronic pain is perceived for a minimum time of about thirty minutes to thereby induce a permanent chronic pain relief in the area where the patient perceives chronic pain.

17. A method of treatment of chronic pain to a user having an area of the body that is responsible for the pain comprising the steps of:

applying a first electrode to the body with said first electrode spaced from the area of the body that is responsible for the chronic pain;

applying a second electrode to the body with said second electrode spaced from the area of the body that is responsible for the chronic pain;

applying an electrical signal having a monophasic wave form comprising a series of sequential wave burst cycles comprised of a wave burst and a pause across said electrodes, said wave burst cycle having a frequency of approximately 8 to 10 wave burst cycles per second, said wave burst having individual waves with said individual waves having approximately 13 to 18 waves per wave burst, said electrical signal having a monophasic wave form applied to the body for approximately thirty minutes to relieve the chronic pain in the body after the treatment has been terminated.

18. A method of treatment of chronic pain to a user having an area of the body that is responsible for the pain comprising the steps of:
   applying a first electrode having a diameter of less than 15 millimeters to the body with said first electrode spaced from the area of the body that is responsible for the chronic pain;
   applying a second electrode having a diameter of less than 15 millimeters to the body with said second electrode spaced from the area of the body that is responsible for the chronic pain;
   applying an electrical signal having a monophasic wave form comprising a series of sequential wave burst cycles, said wave burst cycles including a wave burst having individual waves each having a positive pulse followed by a negative pulse with each of the sequential wave bursts followed by a pause, said electrical signals having a monophasic wave form directed into the body for a period of time sufficient to relieve the chronic pain in the body after the treatment has been terminated.

19. The method of claim 18 wherein one applies a second circular electrode that has a diameter of approximately less than 15 millimeters.

* * * * *